United States Patent [19]
Kiessling et al.

[11] Patent Number: 6,022,859
[45] Date of Patent: Feb. 8, 2000

[54] INHIBITORS OF β-AMYLOID TOXICITY

[75] Inventors: Laura L. Kiessling; Regina M. Murphy, both of Madison, Wis.

[73] Assignee: Wisconsin Alumni Research Foundation, Madison, Wis.

[21] Appl. No.: 08/970,833

[22] Filed: Nov. 14, 1997

Related U.S. Application Data

[60] Provisional application No. 60/030,840, Nov. 15, 1996.

[51] Int. Cl.$^7$ ...................................... A61K 38/00
[52] U.S. Cl. .................. 514/14; 514/13; 514/15; 530/326; 530/327
[58] Field of Search ................... 530/326–327; 514/13–15

[56] References Cited

U.S. PATENT DOCUMENTS 5,716,614  2/1998  Katz et al. .............................. 424/94.3

FOREIGN PATENT DOCUMENTS

WO 94/25043  11/1994  WIPO .
WO 95/20973  8/1995  WIPO .
WO 95/31210  11/1995  WIPO .
WO 96/28471  9/1996  WIPO .

OTHER PUBLICATIONS

Jyothi Ghanta, et al., "A Strategy for Designing Inhibitors of β–Amyloid Toxicity," *J. Biol. Chem.* 271(47):29525029528, 1996.

Lars O. Tjernberg, et al., "Arrest of β–Amyloid Fibril Formation by a Pentapeptide Ligand," *J. Biol. Chem.* 271 (15):8545–8548, 1996.

Dayhoff et al., Atlas of Protein Sequence and Structure (1972) vol. 5 pp. 89–99.

Hughes et al., Proc. Nat'l. Acad. Sci. USA vol. 93 pp. 2065–2070, (Mar. 1996).

*Primary Examiner*—Bennett Celsa
*Attorney, Agent, or Firm*—Quarles & Brady LLP

[57] ABSTRACT

A β-amyloid inhibitor is disclosed. In one embodiment, this inhibitor comprises a recognition element that interacts specifically with β-amyloid peptide and a disrupting element that alters β-amyloid aggregation. In a preferable form of the present invention, the inhibitor is a peptide.

6 Claims, 4 Drawing Sheets

INHIBITORS OF β-AMYLOID TOXICITY

CROSS-REFERENCE TO RELATED APPLICATION

This application claims priority to provisional application 60/030,840 filed Nov. 15, 1996.

This invention was made with the United States government support awarded by the following agencies: NSF, Grant No: BES9067661. The United States Government has certain rights in this invention.

STATEMENT REGARDING FEDERALLY SPONSORED RESEARCH OR DEVELOPMENT

Not applicable.

BACKGROUND OF THE INVENTION

β-amyloid peptide (Aβ) is the major protein component of senile plaques and cerebrovascular amyloid deposits from Alzheimer disease (AD) patients (Glenner, G. G., and Wong, C. W., *Biochem. Biophys. Res. Comm.* 120:885–890, 1984; Wong, C. W., et al., *Proc. Natl. Acad. Sci. USA.* 82:8729–87322, 1985). Deposition of Aβ in the form of amyloid fibrils is believed by many to be causally linked to the disease (Joachim, C. L., and Selkoe, D. J., *Alzheimer Dis. Assoc. Disord.* 6:7–34, 1992). Aβ is toxic to cultured neuronal cells, and this toxicity has been linked to the aggregational and/or conformational status of the peptide (Pike, D. J., et al., *J. Neurosci.* 13:1676–1687, 1993; Simmons, L. K., et al., *Mol. Pharmacol.* 45:373–379, 1994; Ueda, K., et al., Brain Res. 639:240–244, 1994).

Under physiological conditions, Aβ readily aggregates into fibrils with a cross-β sheet conformation. Coincident with the conversion of monomeric Aβ to fibrillar Aβ is a transition from random coil to β-sheet (Terzi, E., et al., *J. Mol. Biol.* 633–642, 1995). Several features of Aβ affect the facility of this transition. The peptide is amphophilic, with a hydrophilic N-terminus and hydrophobic C-terminus; the length of the latter affects the rate of aggregate formation (Jarrett, J. T., et al., *Biochemistry* 32:4693–4697, 1993). In addition, a short hydrophobic stretch at residues 17–21 appears to be critical in the formation of fibrillar structure (Hilbich, C., et al., *J. Mol. Biol.* 228:460–473, 1992; Fraser, P. E., et al., *Biophys. J.* 60:1190–1201, 1991), with charged residues adjacent to this region also contributing to fibril formation (Hilbich, C., et al., supra, 1992; Fraser, P. E., et al., *J. Mol. Biol.* 244:64–73, 1994).

Aggregation likely proceeds via formation of a "nucleus" to initiate fibril formation followed by fibril elongation (Jarrett, J. T., et al., supra, 1993; Shen, C.-L., and Murphy, R. M. *Biophys. J.* 69:640–651, 1995; Lomakin, A., et al., *Proc. Natl. Acad. Sci. USA* 93:1125–1129, 1996).

One strategy for developing lead candidates for drugs to treat AD patients is to screen for small-molecule compounds that disrupt Aβ aggregation and thereby, presumably, interfere with its toxicity. Sulfonated dyes such as Congo red and related sulfonate anions reportedly disrupt Aβ aggregation and reduce Aβ toxicity (Pollack, S. J., et al., *Neurosci. Lett.* 197:211–214, 1995; Kisilevsky, R., et al., *Nature Medicine* 1:143–148, 1995). The cationic surfactant hexadecyl-N-methylpiperidinium bromide inhibits Aβ fibril formation, possibly by binding to a site on Aβ necessary for Aβ self-assembly (Wood, S. J., et al., *J. Biol. Chem.* 271:4086–4092, 1996). β-Cyclodextrin, which has an affinity for hydrophobic groups, partially reduces Aβ toxicity (Camilleri, P., et al., *FEBS Letts* 341:256–258, 1994).

An alternative approach is to use a fragment of Aβ to disrupt Aβ fibril formation. Recently, it was reported that a pentapeptide KLVFF, containing the 16–20 sequence of full-length Aβ, binds to and disrupts fibril formation (Tjernberg, L. O., et al., *J. Biol. Chem.* 271(15):8545–8548, 1996). An octapeptide, QKLVTTAE, with substitutions for the two Phe residues at positions 19 and 20, inhibited fibril formation at a 10-fold molar excess, a result that was attributed to weak interactions between the octapeptide and monomeric Aβ (Hughes, S. R., et al., *Proc. Natl. Acad. Sci. USA* 93:2065–2070, 1996). In both cases, fibril inhibition was assessed by electron microscopy. Effects of the peptide fragments on Aβ toxicity were not reported.

Needed in the art is an improved inhibitor of β-amyloid toxicity.

BRIEF SUMMARY OF THE INVENTION

In one embodiment, the present invention is a β-amyloid inhibitor comprising a recognition element and a disrupting element. The recognition element interacts specifically with β-amyloid peptide (Aβ) and the disrupting element is polar and alters Aβ aggregation.

In one embodiment of the present invention, the inhibitor is a peptide. In a preferred form, the recognition element comprises the amino acid sequence KLVFF (SEQ ID NO:2). In another preferred form, the disrupting element is a sequence of polar charged amino acids, preferably polylysine and most preferably a sequence of six lysines, appended to the C-terminal end of the recognition element.

It is an object of the present invention to provide a compound that disrupts β-amyloid aggregation and interferes with its toxicity, thereby providing a therapeutic reagent for treating Alzheimer disease patients. Preferably, the disrupting element alters the aggregation kinetics and morphology of the β-amyloid aggregate.

Other objects, features and advantage of the present invention will become apparent after review of the specification claims and drawings.

BRIEF DESCRIPTION OF THE SEVERAL VIEWS OF THE DRAWINGS

FIG. 2A graphs co-incubation with recognition peptides.

DETAILED DESCRIPTION OF THE INVENTION

In General

Figure 1:
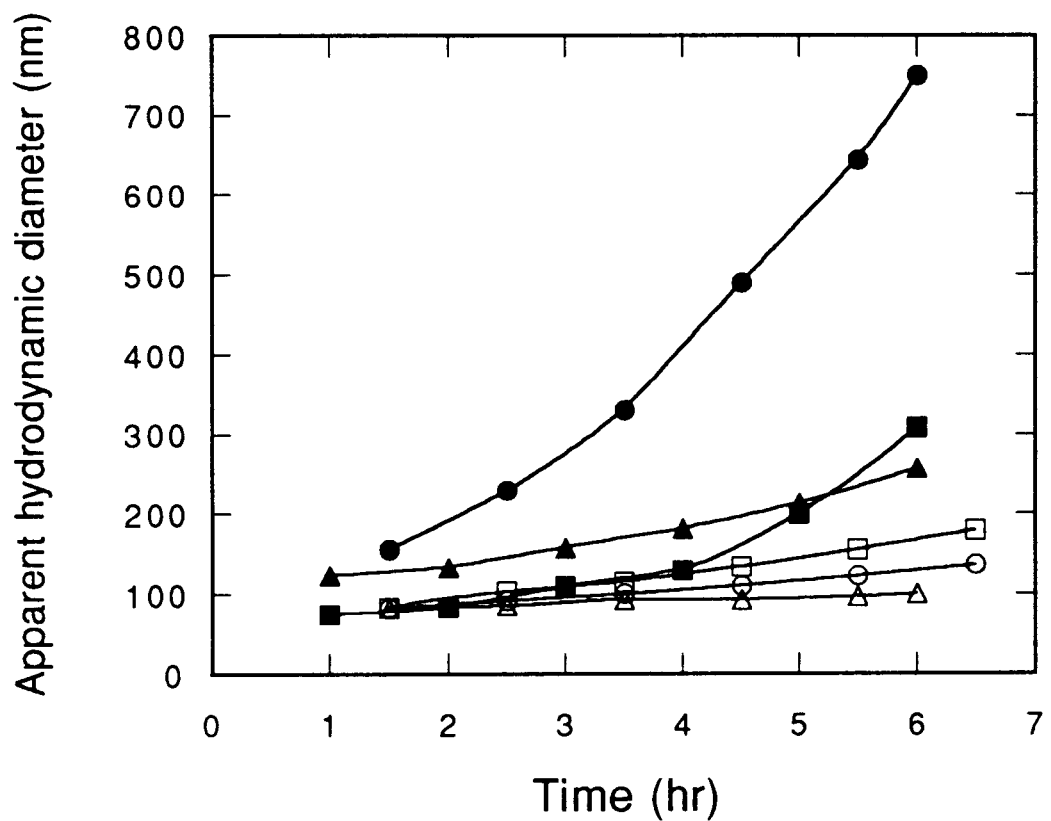
FIG. 1 is a graph of the effect of recognition and hybrid peptides on Aβ(1–39) aggregation.

β-amyloid peptide is the major protein component of Alzheimer's plaques. When aggregated into amyloid fibrils, the peptide is toxic to neuronal cells.

An inhibitor of β-amyloid toxicity is described herein. A recognition element, which interacts specifically with β-amyloid, is combined with a disrupting element, which alters β-amyloid aggregation pathways. In the Examples below, the synthesis, biophysical characterization, and biological activity of two exemplary inhibitors is reported.

One preferable form of the inhibitor described in the examples is composed of residues 15–25 of the β-amyloid peptide, designed to function as the recognition element, linked to a disrupting element. Another preferable form of the inhibitor described in the examples is composed of residues 16–20 of the β-amyloid peptide, designed to function as the recognition element, linked to a disrupting element. Preferably, the disrupting element in these embodiments is oligolysine.

Preferably, the inhibitor of the present invention alters the morphology or kinetics of β-amyloid aggregates or alters its aggregation pathway. In a preferred embodiment, the inhibitor causes changes in aggregation kinetics and higher-order structural characteristics of the aggregate. In an especially preferred embodiment, the inhibitor causes increases in the rate of growth of Aβ fibrillar aggregates from linear to more branched or entangled structures. Evidence for these effects would include changes in aggregation kinetics and aggregate morphology observed by light scattering and electron microscopy.

In addition to its influence on the physical properties of β-amyloid aggregates, a preferable inhibitor completely blocks β-amyloid toxicity to PC-12 cells. Together, the data suggest that this general strategy for design of β-amyloid toxicity inhibitors is effective. Significantly, these results demonstrate that complete disruption of amyloid fibril formation is not necessary for abrogation of toxicity.

Recognition Elements

The Examples below describe an inhibitor comprising residues 15–25 of the β-amyloid peptide. However, other suitable recognition elements are envisioned.

It is necessary that the recognition element specifically recognize the full-length peptide.

By "specifically recognize" it is meant that the recognition element binds to a portion of the β-amyloid peptide with a binding affinity of at least $10^4$ $M^{-1}$, or preferably greater, and further that a scrambled sequence (e.g., an element containing the identical amino acid constituents but in a different sequence than that of β-amyloid) would bind with a weaker affinity or not at all, and further that the recognition element would bind with a weaker affinity or not at all to proteins which are not β-amyloid.

An important concern in the choice of the recognition element is that it should interact specifically with Aβ but not with itself. In designing a recognition element, one would preferably focus on regions of β-amyloid that are believed to be essential to fibril formation. One example of such a region is the C-terminal sequence, which is known to play an important role in formation and stability of a β-amyloid fibrils. The C-terminal sequence plays an important role in the formation and stability of Aβ amyloid fibrils (Jarrett, J. T., et al., supra, 1993). This sequence, however, is highly hydrophobic and aggregates rapidly (Halverson, K., et al., Biochemistry 29:2639–2644, 1990); therefore, it would not be a preferred recognition element. Several lines of evidence show that the interior sequence 17–23 is crucial to formation of cross-β fibrils (Terzi, E., et al., supra, 1995; Hilbich, C., et al., supra, 1992; Fraser, P. E., et al., supra, 1991; Wood, S. J., et al., Biochemistry 34:724–730, 1995; Lee, J. P., et al., Biochemistry 34:5191–5200, 1995). We chose the sequence 15–25 as our exemplary recognition element.

We envision that any contiguous sequence comprising at least four residues, and preferably at least five residues, of residues 15–25 of the Aβ sequence would be suitable. Preferably, the four (or five) residues would be chosen from residues 16–23. Most preferably, the residues would comprise residues 16–20.

To obtain a peptide recognition element, one could synthesize through conventional solid phase peptide synthesis or purchase a synthetic peptide or obtain the peptide through recombinant genetic engineering.

We also envision that molecules that mimic the contiguous sequence described above would be suitable. Because the recognition element may interact with Aβ through the formation of beta strand structures, molecules that can adopt such a structure are preferred. Specifically, suitable mimics include pyrrolidine-based inhibitors with side chains corresponding to those in the peptide recognition element (e.g., Smith, A. B., et al., J. Am. Chem. Soc. 117:1113–1123, 1995).

Suitable recognition elements can contain amino acids other than the 20 that are genetically encoded. For example, naphthylalanine, D-α-methylalanyl and L-α-methylalanyl can substitute for phenylalanine. Other groups that can substitute for phenylalamine residues in the recognition sequence include the furazanyl, furyl, immidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

For alkyl amino acids, such as leucine or valine, other side chains such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Other possible recognition elements include synthetic peptides synthesized from D-amino acids, having the same contiguous sequence as described above or in reverse order.

Disruption Elements

We envisioned that attachment of polar, hydrophilic functionality to the recognition element would afford a molecule that could bind to Aβ and alter Aβ aggregation kinetics and/or Aβ aggregate morphology. Preferably, the attachment is at the C-terminus of the recognition element.

To test this hypothesis, we chose to add a sequence of lysine residues to the Aβ binding sequence. The Examples below describe this disrupting element comprised of oligolysine. The element was selected because it was reasoned that an attachment of polar hydrophilic groups through the recognition element would prevent an elongation of the beta structures formed in amyloid fibrils.

However, we believe that other disrupting elements would be equally suitable. For example, a disrupting element could be another chain of polar amino acids and could be composed of either peptides and nonpeptides or a combination of both.

In addition to polar amino acid residues, disrupting elements can also be composed of residues that interfere with beta sheet formation, such as proline residues or N-methylated amino acid residues. The disrupting element can contain amino acids other than the 20 genetically encoded amino acids. For example, the polar L-α-hydroxylysyl and isoquinolyl amino acids can be incorporated into disrupting elements. Other possible disrupting elements include saccharides, oligosaccharides, or other hydrophilic molecules that can be chemically conjugated to the recognition element.

Features of Hybrid Inhibitors The peptidic compounds of the present invention also serve as structural models for non-peptidic molecules with similar biological activity. One can also readily modify peptides by phosphorylation, and other methods for making peptide derivatives of the compounds of the present invention are described in Hruby, et al. *Biochm. J.* 268(2):249–262, 1990, incorporated herewith by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor, *Ann. Rep. Med. Chem.* 24:243–252, 1989, incorporated herein by reference. These techniques include replacing the peptide backbone with a backbone composed of phosphonates, amidates, carbamates, sulfonamides, and secondary amines.

Evaluation of Combinations

If one wishes to evaluate a specific recognition element/disruption element combination, one would preferably evaluate the inhibitor by the methods described below in the Examples. The Examples describe light scattering, electron microscopy, and cellular toxicity. Preferably, a suitable inhibitor of the present invention will perform as well as the exemplary inhibitor described below in the Examples by all three parameters. However, we envision that a suitable inhibitor does not necessarily have to be as successful as our exemplary inhibitor.

A suitable inhibitor should completely prevent toxicity in the MTT assay at a 2:1 (inhibitor to A$\beta$) molar ratio or lower.

We also envision that light scattering methods could be used to evaluate the combination. Preferably, the method would be used and evaluated as follows: suitable inhibitors would change, and most preferably increase, the rate of A$\beta$ aggregate growth as assessed by dynamic light scattering and would change the aggregate morphology as assessed by static light scattering, most preferably by changing the morphology from a more linear to a more branched or entangled structure.

Of course, one would ultimately examine the inhibitors in assays designed to accurately predict whether a particular inhibitor would be useful for Alzheimer's disease treatment. We envision that if an inhibitor passed the cellular toxicity assay, one would want to evaluate the inhibitor with primary neuronal cultures and, possibly, transgenic mouse models.

Therapeutic Formulation

We envision that one would use the inhibitor of the present invention as an Alzheimer's disease therapeutic. If the inhibitor were peptide in nature, one could use a gene therapy technique to deliver DNA constructs encoding the inhibitor to the affected sites. For drug formulations, one would expect that the formulations reach and be effective at the affected site. These inhibitors would more likely be carbohydrate and peptide mixtures, especially mixtures capable of overcoming the blood brain barrier. For examples, see Tamai, et al., *Adv. Drug Delivery Reviews* 19:401–424, 1996, hereby incorporated by reference. In these cases, the disrupting element of the inhibitor would also facilitate transport across the blood-brain barrier.

Thus, the present invention encompasses methods for therapeutic treatment of Alzheimer's disease that comprise administering a compound of the invention in amounts sufficient to alter the aggregation of A$\beta$ into fibrils.

Accordingly, the present invention includes pharmaceutical compositions comprising, as an active ingredient, at least one of the peptides or other compounds of the invention in association with a pharmaceutical carrier or diluent. The compounds of the invention can be administered by oral, parenteral (intramuscular, intraperitoneal, intravenous (IV) or subcutaneous injection), transdermal, nasal, vaginal, rectal, or sublingual routes of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filters, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration area are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired.

EXAMPLES

We report a new strategy for generating molecules that interfere with A$\beta$ toxicity. This approach relies on two features of A$\beta$: it is a self-recognizing peptide, and its toxicity depends on it adopting a specific conformational and/or aggregational state. Therefore, attachment of a short fragment of A$\beta$, which can specifically recognize the full-length peptide, to a disrupting element, which functions to alter A$\beta$ aggregation, may afford a new molecule capable of ameliorating the toxicity of A$\beta$. To test the feasibility of this approach, we synthesized several such hybrid compounds. We found that these inhibitors not only alter A$\beta$ aggregation, but also block A$\beta$ toxicity in vitro.

The following abbreviations are used herein: A$\beta$, $\beta$-amyloid peptide; ACN, acetonitrile; HPLC, high pressure liquid chromatography; MTT, 3-(4,5-dimethylthiazol-2-yl)-2,5-diphenyltetrazolium bromide; PBS, phosphate-buffered saline; PBSA, PBS with azide; TFA, trifluoroacetic acid; ThT, thioflavin T.

A. Experimental Procedures

Peptide Synthesis and Purification

A peptide homologous to the first 39 residues of Aβ, Aβ(1–39), was purchased from AnaSpec, Inc. (San Jose, Calif.) and was described previously (Shen, C.-L., and Murphy, R. M., supra, 1995). A peptide homologous to the 25–35 residues of Aβ, Aβ(25–35), was purchased from Sigma (St. Louis, Mo.)

Six "recognition" peptides, containing recognition elements only, and four "hybrid" peptides, combining recognition with disrupting elements, were synthesized. Table 1 summarizes the sequence and characterization of these peptides. For the recognition peptides, the nomenclature refers to the homologous sequence in the full-length Aβ. For the hybrid peptides, "recognition" elements which are homologous to a section of Aβ are shown in bold; "disrupting" elements are italicized.

All peptides except 15-25-K6 and K6-15-25 were synthesized using standard solid-phase methods. The peptides were purified by reverse-phase HPLC on a Vydac C-18 column using a 20%–100% linear gradient of acetonitrile/water with 0.1% TFA as the mobile phase. Analysis by mass spectrometry using a VG AutoSpec M (LSIMS) afforded measured molecular masses close to the theoretical molecular mass, as listed in Table 1.

Hybrid peptides 15-25-K6 and K6-15-25 were synthesized by Anaspec (San Jose, Calif.). These peptides were purified by reverse-phase HPLC, and their purity was estimated from the chromatogram to be >96%. Mass spectroscopy of K6-15-25 revealed a molecular mass close to its theoretical value. Analysis of 15-25-K6 suggested that it was a mixture with a major component having the expected molecular mass and a minor component with a slightly lower molecular mass, likely corresponding to a des-Gln contaminant that was not resolvable by HPLC.

Peptides were stored in lyophilized form at −70° C.

Circular Dichroism Spectroscopy

β(1–39), 15-25-K6, or a mixture of β(1–39) and 15-25-K6 (1:2 molar ratio) were dissolved in 0.01 M phosphate buffer, pH 7.2. The final concentration was 0.5 mg/ml for each peptide. The solution was passed through a 0.45 μm Millipore (Bedford, Mass.) filter to remove dust and then degassed. Circular dichroism spectra in the far UV (190–240 nm) were obtained using a modified Cary Model 60 spectropolarimeter (On-line Instrument Systems, Bogart, Calif.) and analyzed for secondary structure as described (Shen, C.-L., et al., *Biophys. J.* 65:2383–2395, 1993).

Dynamic Light Scattering

Lyophilized Aβ(1–39) was solubilized in 0.1% TFA at 10 mg/ml, then diluted twenty-fold into PBSA or into PBSA containing the test peptide. PBSA was double-filtered through a 0.22 μm filter prior to use. pH was adjusted to 7.4 with 0.5 N NaOH, then the sample was immediately filtered through a 0.45 μm filter directly into a clean light scattering cuvette. In all cases Aβ(1–39) concentration was 0.5 mg/ml and the molar ratio of test peptide to Aβ was 2:1 unless otherwise indicated. Autocorrelation functions at 90° scattering angle were collected as described previously (Shen, et al., 1994, supra). Data were fit using the method of cumulants to derive and apparent hydrodynamic radius.

Static Light Scattering

Solutions of Aβ(1–39) alone or with test peptide at a 2:1 peptide:Aβ molar ratio were prepared as described above. Solutions were incubated at room temperature for 24 hours, after which scattered intensity data as a function of angle were collected and analyzed as described elsewhere (Shen, C.-L. and Murphy, *Biophys. J.*, 1995, supra).

Electron Microscopy

Solutions of Aβ(1–39) alone (0.5 mg/ml) or with 1 mg/ml 15-25-K6 were prepared as described above and aged at room temperature for approximately one week. A drop of the peptide solution was placed on a Pioloform coated 300 mesh electron microscope copper grid. After blotting, a drop of 1% ammonium molybdate was placed on the grid while being held with fine forceps. The grid was blotted on filter paper and allowed to dry before observing the specimen in a JEOL (Peabody, Mass.) 100 CX Electron Microscope at 60 kV.

TABLE 1

Peptides Tested

| Name | Sequence | Theor. mass | Meas. mass | Soluble |
|---|---|---|---|---|
| Recognition peptides | | | | |
| 16-19 | KLVF (SEQ ID NO: 1) | 505.7 | 506.3 | yes |
| 16-20 | KLVFF (SEQ ID NO: 2) | 652.8 | 653.4 | yes |
| 16-25 | KLVFFAEDVG (SEQ ID NO: 3) | 1124.4 | 1125.3 | no |
| 18-25 | VFFAEDVG (SEQ ID NO: 4) | 883.0 | 883.5 | yes |
| 19-25 | FFAEDVG (SEQ ID NO: 5) | 783.8 | 784.4 | yes |
| 20-25 | FAEDVG (SEQ ID NO: 6) | 636.7 | 637.4 | yes |
| Control recognition peptide | | | | |
| 16-20S | VLFKF (SEQ ID NO: 7) | 652.8 | 653.4 | yes |
| Hybrid peptides | | | | |
| 16-20-K5 | KLVFFKKKKK (SEQ ID NO: 8) | 1421.93 | 1422.0 | yes |
| 20-25-K6 | FAEDVGKKKKKK (SEQ ID NO: 9) | 1406 | 1405.4 | yes |
| 15-25-K6[a] | GQKLVFFAEDVGGaKKKKKK (SEQ ID NO: 10) | 2192.7 | 2190.3, 2062.6 | yes |
| K6-15-25 | KKKKKKGGQKLVFFAEDVG (SEQ ID NO: 11) | 2136.6 | 2136.1 | |

[a]The "a" in the sequence indicates an aminocaproate linker.

Cellular Toxicity

Solutions of recognition or hybrid peptides were prepared by direct dissolution of lyophilized peptide into sterile PBS (with antibiotics). Aβ(1–39) was dissolved in 0.1% TFA at 10 mg/ml, then diluted twenty-fold into sterile PBS (with antibiotics) or PBS containing the hybrid or recognition peptides. Solutions were prepared at 2:1 or 1:1 peptide:Aβ molar ratio. The samples were incubated at room temperature for 7 days, then diluted five-fold with medium and incubated for one day. As a control, PBS was diluted 5:1 with medium and added to some wells.

ThT Fluorescence Spectroscopy

A few samples used for cellular toxicity assays were tested for ThT fluorescence after one week aging and prior to dilution into cell culture medium. ThT (Sigma, St. Louis, Mo.) was dissolved at 100 μM in PBSA. Forty μl peptide solution and 40 μl ThT stock solution were mixed with 920 μl PBSA and briefly vortexed. Fluorescence emission spectra were taken using a Model M-3 Alphascan (Photon Technology International, South Brunswick, N.J.) spectrofluorimeter, with excitation at 450 nm. An increase in fluorescence with a maximum at 482 nm is indicative of amyloid (LeVine, H. *Protein Sci.* 2:404–410, 1993). Fluorescence intensity for diluted ThT in the absence of peptide was determined and subtracted from sample intensities.

B. Results

Solubility, Conformational, and Aggregation Properties of Aβ-related Peptides Alone and with Aβ(1–39)

Circular dichroism spectra of Aβ(1–39) and 15-25-K6 in phosphate buffer (0.1 M, pH 7.4) were collected and quantitatively analyzed for secondary structure. Aβ(1–39) was 65% β-sheet and 30% random coil (spectra not shown), in line with previous measurements (Shen, C.-L., et al., supra, 1994). The secondary structure of 15-25-K6 was essentially the same (64% Aβ-sheet, 36% random coil, data not shown). 15-25-K6 did not significantly alter circular dichroism spectra of Aβ(1–39) (not shown); quantitative analysis was not attempted due to some turbidity of the mixture.

The solubility and aggregation properties of the test peptides were assessed by visual observation, analytical ultracentrifugation, and/or dynamic light scattering. Of the recognition peptides listed in Table 1, only 16–25 was insoluble in PBSA. 16-20, 18-25, and 20-25 were all monomeric, as determined by sedimentation equilibrium ultracentrifugation. Of the hybrid peptides, 16-20-K6, 20-25-K6, and 15-25-K6 were all readily soluble in PBSA. By ultracentrifugation, 15-25-K6 was monomeric (the others were not tested). None of the solutions of these three hybrid peptides scattered light above background levels (100 mW argon ion laser incident beam, detected by photomultiplier tube at 90° scattering angle), indicating that there was no significant aggregation. Although initially soluble in PBSA, K6-15-25 aggregated rapidly and precipitated; this peptide was not tested further.

The effect of the test peptides on aggregation kinetics of Aβ(1–39) was assessed by dynamic light scattering (FIG. 1). FIG. 1 graphs the effect of recognition and hybrid peptides on Aβ aggregation kinetics. Final Aβ concentration was 0.5 mg/ml, Aβ:peptide molar ratio was 1:2 except where indicated. The hydrodynamic radius (measured at a 90° scattering angle) was measured as a function of time.

Referring to FIG. 1, there was a measurable increase in the size of Aβ aggregates with time (open circles). Recognition peptides 16–20 (open triangle) or 20–25 (open square) had no effect on the aggregate size or growth rate. Hybrid peptide 20-25-K6 (solid square) had at most a modest effect on aggregate growth rate. In contrast, hybrid peptide 15-25-K6 (solid circle) caused a dramatic increase in the growth rate. By far the greatest effect on growth rate was observed with 16-20-K6. At the 2:1 peptide:Aβ molar ratio used for the other solutions, the growth rate was too fast to be measured. The concentration of 16-20-K6 was reduced four-fold and these data are shown in FIG. 1 (solid triangle). There was still a substantial effect on aggregate size and growth rate at this much-reduced molar ratio.

The effect of the test peptide on aggregate size and morphology was probed with static light scattering. Briefly, the intensity of scattered light extrapolated to zero scattering angle yields information on the average molecular weight of the aggregate, while the angular dependence of the scattered light intensity reveals information about the aggregate shape and characteristic dimensions. Recognition peptides 18–25 and 20–25 had no effect on the average apparent molecular weight of Aβ(1–39) 24 hours after mixing, whereas addition of 16–20 to Aβ(1–39) apparently resulted in a modest (~two-fold) increase in molecular weight. Of the three hybrid peptides, 20-25-K6 had no observable effect on the average molecular weight of Aβ aggregates, whereas 15-25-K6 and 16-20-K6 both caused ~2–2.5-fold increase in molecular weight. Thus, the average molecular weight of Aβ(1–39) aggregates was not dramatically affected by any of the peptides tested.

Figure 2A:
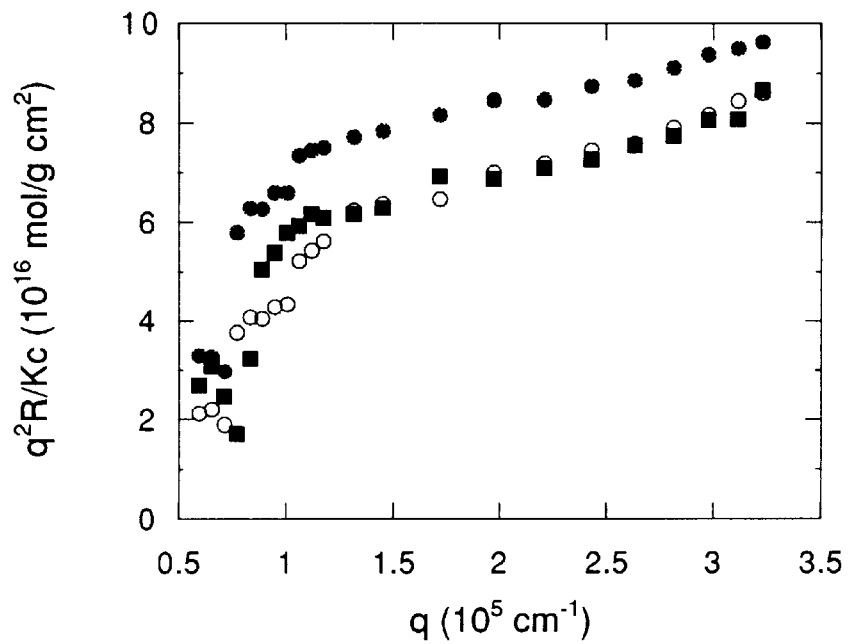
FIGS. 2A and B are Kratky plots of Aβ-peptide solution.
Figure 2B:
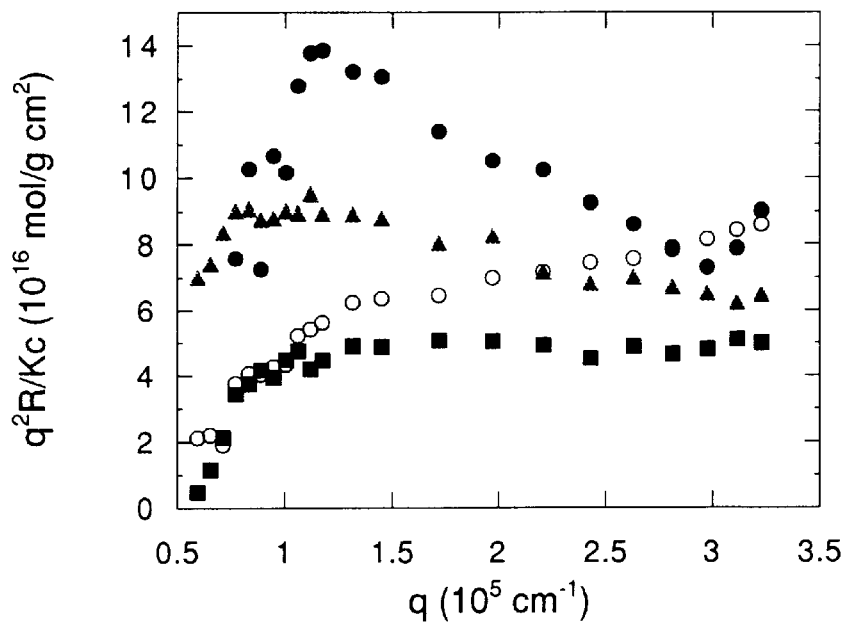
FIG. 2B graphs co-incubation with hybrid peptides.

A convenient tool for abstracting particle shape information from angular dependence data is the so-called Kratky plot. FIGS. 2A and B are Kratky plots of Aβ-peptide solutions. Aβ(1–39) was co-incubated with recognition (A) or hybrid (B) peptides for 24 hours, after which SLS data were collected, analyzed, and plotted as Kratky plots. In all cases, Aβ(1–39) concentration was 0.5 mg/ml and the peptide:Aβ molar ratio was 2:1, except for 16-20-K6 for which the molar ratio was lowered to 1:2. In FIG. 2, q is the scattering vector, which is related to the scattering angle, R is the Rayleigh ratio, a function of the scattering intensity, c is the concentration, and K is an instrument constant. Referring to FIG. 2A, the rising curves with an intermediate plateau are characteristic of semiflexible linear chains. There is no difference observed between Aβ(1–39) alone (open circles) or with 18–25 (solid squares). The displacement of the curve upward for Aβ(1–39) with 16–20 (solid circles) relative to Aβ(1–39) alone is indicative of an increase in aggregate molecular weight with no change in aggregate shape. Referring to FIG. 2B, the "bump" at intermediate values of q is characteristic of branched structures; with the height of the bump indicative of the degree of branching.

Referring to FIG. 2A, Aβ(1–39) alone, or co-incubated with the recognition peptides, formed linear semiflexible aggregates (typical for fibrils). Referring to FIG. 2B, when Aβ(1–39) was incubated with any of the three hybrid peptides, there was a clear change in the morphology of the aggregate, to a shape consistent with a branched or entangled structure. Overall, 20-25-K6 (solid squares) had the least effect on Aβ(1–39), with no statistically significant change in molecular weight and a modest change in particle shape. 15-25-K6 (solid circles) and 16-20-K6 (solid triangles) both increased the average molecular weights of the Aβ(1–39) aggregates; 15-25-K6 appeared to have the greatest effect on the particle shape, but the data for 16-20-K6 were taken at a four-fold lower concentration of the hybrid peptide without changing the concentration of Aβ(1–39) so the comparison is not direct. Thus, addition of the hexameric lysine disrupting element invariably caused a change in morphology from linear to more branched.

ThT fluorescence intensity was measured for Aβ-amyloid (1–39) alone or mixed with 18–25 or 15-25-K6 after one week incubation at room temperature. Samples were diluted 25-fold just prior to measurement. 15-25-K6 reduced the ThT fluorescence intensity of Aβ(1–39) somewhat (data not shown). Because 16–25 was not soluble in PBS, the assay could not be repeated in a like manner for that peptide; however, a parallel experiment was conducted by dissolution of 16–25 or 18–25 into 35% ACN/TFA followed by mixing with Aβ(1–39) and dilution into PBS. The increase in ThT fluorescence for these samples was comparable to that observed using the first protocol (data not shown). Aβ(25–35) alone caused a substantial increase in ThT fluorescence intensity; mixing 15-25-K6 with β(25–35) had neither a positive nor a negative effect on ThT fluorescence (data not shown).

Figure 3A:
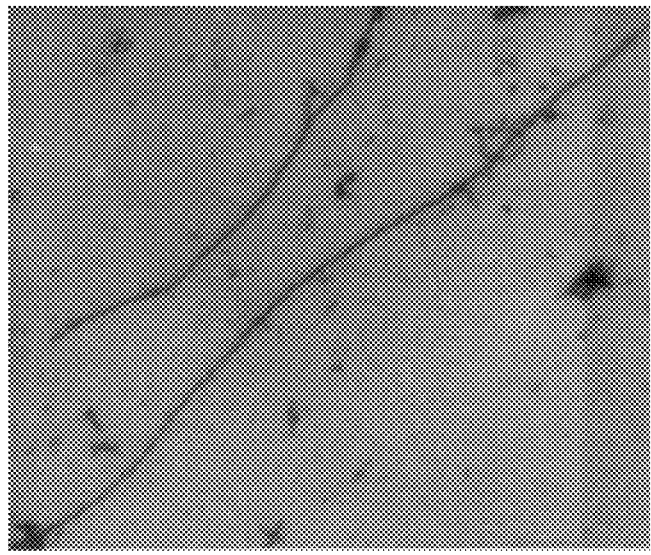
FIGS. 3A and B are electron micrographs of (A) Aβ(1–39) alone and (B) Aβ(1–39) with 15-25-K6.

To further examine the aggregates, electron micrographs were taken. FIG. 3A and B are electron micrographs of (A) Aβ(1–39) alone and (B) Aβ(1–39) with 15-25-K6. Magnification is 72,500x.

Figure 3B:
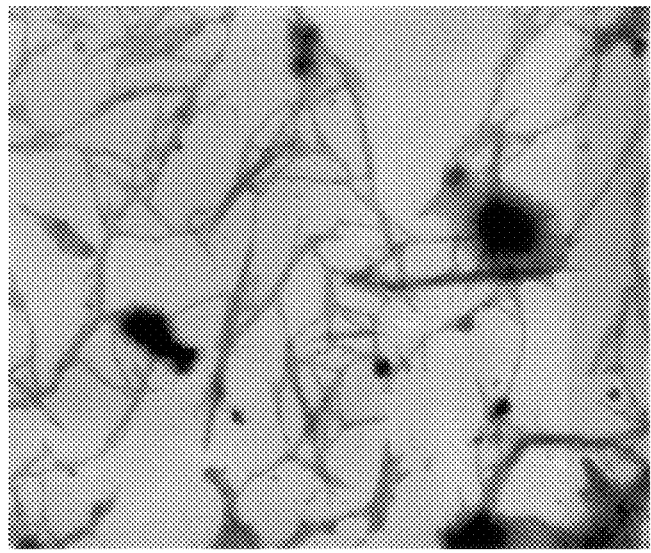

Aβ(1–39) formed characteristic long, semiflexible fibrils (FIG. 3A). Mixing 16–25 with Aβ(1–39) had no obvious effects on fibril morphology (not shown). Addition of 15-25-K6 to Aβ(1–39) did not prevent fibril formation but did appear to reduce the average length of fibrils, and increase the extent of fibril entanglement, compared to Aβ(1–39) alone (FIG. 3B).

C. Effect of Synthetic Peptide on Aβ(1–39) Toxicity

Figure 4A:
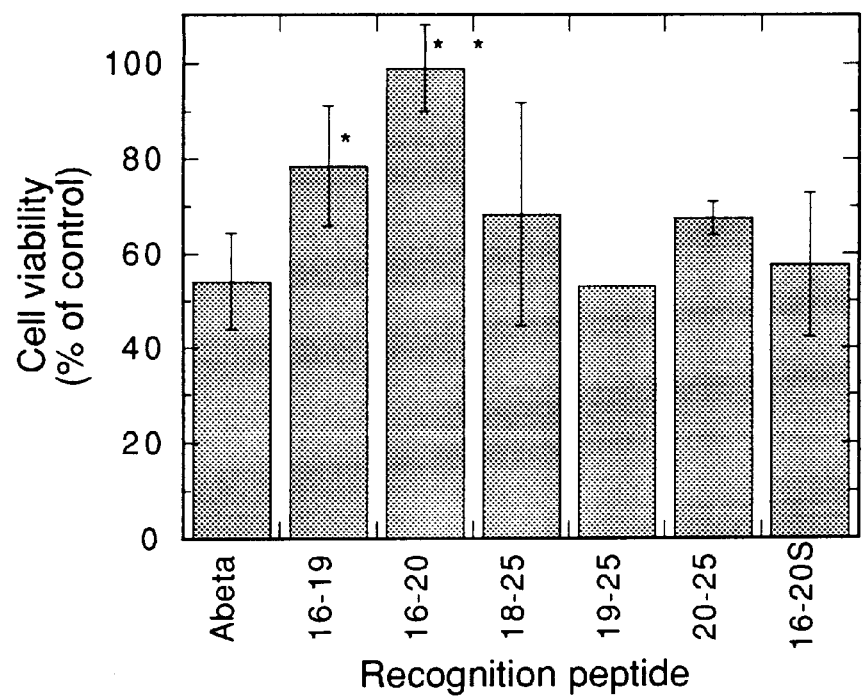
FIGS. 4A and B are bar charts demonstrating the toxicity of Aβ-related peptides mixed with Aβ(1–39). Aβ was incubated with recognition peptides (FIG. 4A) or hybrid peptides (FIG. 4B).
Figure 4B:
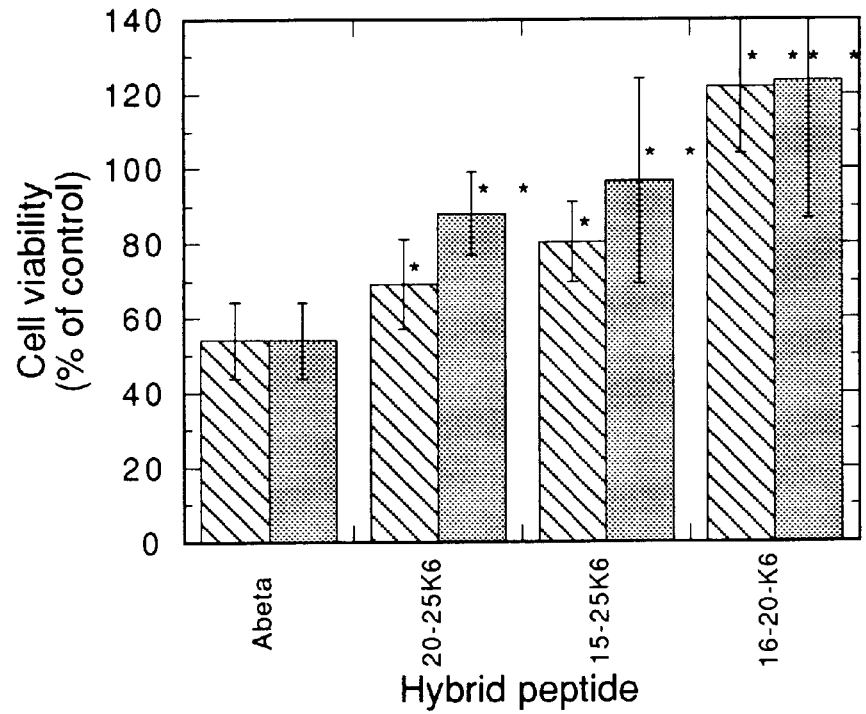

Freshly-prepared solutions of Aβ(1–39) were not toxic to the cells, consistent with other reports in the literature (Shearman, et al., supra). None of the test peptides alone were toxic. FIG. 4 is a bar chart demonstrating the effect of mixing the test peptides with Aβ(1–39) on toxicity. FIG. 4 graphs the effect of recognition and hybrid peptides on Aβ toxicity. Aβ(0.5 mg/ml) was incubated with the recognition peptide at a 1:2 Aβ:peptide molar ratio (A), or with the hybrid peptides at a 1:1 or 1:2 Aβ:peptide molar ratio (B), for one week, following which the solution was diluted five-fold and added to monolayer cultures of PC-12 cells. Cell viability was assessed with the MTT assay; results are reported relative to untreated wells. Each bar represents the mean ± s.d. of 1–6 replicate runs (13 replicates for Aβ alone), where each run is the average of five determinations. The ability of each peptide to protect cells from Aβ toxicity was assessed by a upper-tailed t-test; *, $p<0.01$; **, $p<0.001$.

Referring to FIG. 4, toxicity was measured by MTT reduction in PC-12 cells relative to control (PBS). "Aged" Aβ(1–39) alone caused a reduction in cell viability to about 50% of control. Of the recognition peptides, only 16–19 and 16–20 afforded any protection against Aβ(1–39) toxicity, at a 2:1 peptide:Aβ molar ratio. At a 1:1 ratio none of the recognition peptides were effective inhibitors (not shown). Conclusive results with 16–25 could not be obtained since this peptide is insoluble in PBS. The inhibitory action of 16–20 appears to be sequence-specific, since the scrambled sequence peptide 16–20S was not active. All three hybrid peptides offered at least partial inhibition of Aβ toxicity at both molar ratios tested. 16-20-K6 was the most effective, completely protecting cells from Aβ toxicity at both 2:1 and 1:1 molar ratios. 20-25-K6 was least effective, with barely significant protection at the lower ratio. 15-25-K6 was intermediate in protective effect. Thus, addition of the lysine hexamer increased the inhibitory activity (and, in the case of 16–25, the solubililty) of the recognition elements. Taking into consideration both solubility and efficacy, the best recognition element appears to be 16–20. This is consistent with binding studies reported recently by Tjernberg, et al., (Tjernberg, L. O., et al., *J. Biol. Chem.* 271:8545–8548, 1996), in which it was shown that the peptide KKLVFFA interacts with the homologous sequence in Aβ, and that only pentapeptides or longer sequences interacted with Aβ to any significant extent. The oligolysine enhances the protective effect of 16–20, thus, the disrupting element works synergistically with the recognition element.

D. Discussion

We hypothesized that the toxic effects of Aβ might be diminished in the presence of molecules possessing an Aβ recognition element and an amyloid disrupting unit. In the peptides reported here, a short fragment of the self-recognizing peptide Aβ was chosen to mediate specific binding to full-length Aβ. The disrupting element employed, a short stretch of lysine residues, was selected because it was reasoned that attachment of polar hydrophilic groups to the recognition element might prevent elongation of the β-structures formed in amyloid fibrils.

To examine the structural and functional properties of the synthetic peptides, we employed a variety of biophysical measurements including light scattering, circular dichroism spectroscopy, and electron microscopy. For each analytical method, we compared the recognition peptides alone, the hybrid peptides alone, Aβ(1–39) alone, and then recognition or hybrid peptides mixed with Aβ. These measurements were then correlated with cellular toxicity studies.

The solubility and aggregation properties of the recognition peptide 16–25 and the corresponding hybrid peptides K6-15-25 and 15-25-K6, with N- or C-terminal placement of the lysine disrupting domain, were compared. 16–25 by itself was insoluble in PBSA. Addition of the lysine hexamer to either N- or C-terminus resulted in a soluble product. However, whereas 15-25-K6 remained soluble and monomeric, K6-15-25 aggregated rapidly and eventually precipitated. Consequently, the location of the polylysine sequence was found to be a critical feature in the properties of these hybrid peptides, and subsequent hybrid peptides were synthesized with C-terminal placement of the disrupting element. All of the remaining recognition and hybrid peptides in Table 1 were readily soluble in PBSA and did not appear to self-aggregate.

The effect of the recognition and hybrid peptides on conformational and aggregational properties of Aβ(1–39) was assessed. To analyze whether changes in secondary structure occurred, circular dichroism spectra of Aβ(1–39) and 15-25-K6 in phosphate buffer (0.01 M, pH 7) were collected and quantitatively analyzed. The secondary structure of Aβ(1–39) and 15-25-K6 were similar, approximately ⅔ β-sheet and ⅓ random coil, and no significant alterations in circular dichroism spectra were detected for samples in which 15-25-K6 was added to Aβ(1–39). To determine whether changes in aggregation kinetics were observed, dynamic light scattering data were taken over a 6 hour period for solutions of Aβ(1–39) with the recognition or hybrid peptides. These experiments indicated that none of the recognition peptides had a substantial impact on the rate of increase in Aβ aggregate size. In contrast, the hybrid peptides increased the rate of Ab aggregate growth. The smallest effect was observed with 20-25-K6, an intermediate effect with 15-25-K6, and the greatest effect with 16-20-K6. (Note that in the data shown in FIG. 1, the concentration of 16-20-K6 is four-fold lower than that for the other hybrid peptides, so the effect is considerably reduced.) These general trends were confirmed through static light scattering measurements. Aggregates of Aβ alone showed a pattern on a Kratky plot which is classic for semiflexible linear fibrils. The recognition peptides had no significant effect on the morphology of Aβ aggregates, although 16–20 appeared to cause a modest increase in the average size of the aggregates. In contrast, all three hybrid peptides caused a change in Aβ aggregate morphology; the pattern observed was consistent with the presence of branched or entangled structures. In further confirmation of these morphological assignments, electron micrographs demonstrated a linear semiflexible structure of Aβ alone and an entangled mass of shorter fibrils for Aβ with 15-25-K6. Together, these data support the hypothesis that it is the disrupting element which is responsible for the changes in aggregation kinetics and morphology that are observed, but the extent of these changes is controlled by the recognition element. The hybrid peptides do not prevent β-sheet formation or fibril initiation. Rather, they appear to disrupt the fibril elongation process and/or fibril-fibril association processes.

Given the changes in the physical properties of the aggregates formed by Aβ(1–39) induced by the presence of the hybrid peptides, we examined the ability of the hybrid and recognition peptides to modulate the cellular toxicity of "aged" Aβ(1–39), using an MTT reduction assay. A decrease in MTT reduction has been shown to be an early indicator of Aβ-mediated toxicity (Sherman, et al., 1994, supra). None of the recognition or hybrid peptides alone were toxic. Aged Aβ(1–39) caused a decrease in MTT reduction to ~50% of controls. Of the recognition peptides, only 16–19 and 16–20 afforded any protection against Aβ toxicity at a 2:1 peptide:Aβ molar ratio, and none were effective inhibitors at a 1:1 ratio. All three hybrid peptides provided at least partial inhibition of Aβ toxicity at both 2:1 and 1:1 ratios. 16-20-K6 was the most effective, providing complete inhibition of Aβ toxicity at both ratios. 20-25-K6 was the least effective, with barely significant protection at the lower ratio. 15-25-K6 was intermediate in protective effect. Taken together, these data indicate that hybrid peptides with appropriate recognition and disrupting elements can protect cells from Aβ toxicity. The recognition element 20–25 has no inhibitory activity by itself but becomes somewhat protective when the hexameric lysine disrupting element is appended. The oligolysine enhances the protective effect of 16–20, thus, the disrupting element works synergistically with the recognition element. The most effective inhibitory compound required both elements: a recognition element which contains the 16–20 sequence, and the oligolysine disrupting element.

Interestingly, inhibition of Aβ toxicity did not require measurable conformational changes, prevention of fibril formation, or reduction in aggregate growth kinetics. Instead, changes in the Aβ aggregation pathway caused by the hybrid peptides apparently drastically alter the toxicity of Aβ aggregates. This result was unexpected, and suggests a novel mechanism for disrupting Aβ toxicity.

15-25-K6 shares essentially no homology with Aβ(25–35), which also forms fibrillar aggregates and is toxic to cells. Aβ(25–35) decreased MTT reduction to 45% of controls; co-incubation of 15-25-K6 with Aβ(25–35) had no effect on the toxicity of Aβ(25–35). The selective effect of 15-25-K6 on the toxicity of Aβ(1–39), with which the hybrid peptide does share homology, suggests that there is a specific interaction between the recognition element of the inhibitor and a homologous segment of Aβ.

We propose the following interpretation of the combined toxicity and physicochemical data. Recognition peptides 18–25 and 20–25 have no effect on either aggregation or toxicity of Aβ. This likely indicates that these fragments lack sufficient binding affinity for Aβ. Recognition peptide 16–20 may cause a modest increase in the average size of Aβ aggregates without affecting the aggregate morphology, and offers some protection against Aβ toxicity. This suggests that 16–20 is incorporated into the Aβ fibril without causing a major disturbance in the fibrillization pathway; still, the subtle changes occurring during this interaction are sufficient to disrupt Aβ toxicity to some extent. Appending a hexameric lysine disrupting element to any of the recognition elements altered fibril aggregation kinetics and fibril morphology, and provided some protection against Aβ toxicity. These effects were weakest when the oligolysine sequence was attached to 20–25; we propose that this is a consequence of the lack of significant binding affinity of 20–25 for Aβ. The greatest disruption of Aβ aggregation kinetics and aggregate morphology, and the greatest protection from Aβ toxicity, was afforded by the hybrid peptide that combined an effective recognition element, 16–20, with an effective disrupting element, K6.

Work reported here suggests that, by combining appropriate Aβ recognition elements with amyloid disrupting elements, Aβ aggregation pathways are altered and Aβ toxicity is inhibited. Given the successful demonstration of this strategy, we envision 16-20-K6 and 15-25-K6 to be prototypes for the design of inhibitors with improved properties. For example, D-amino acid sequences or organic peptidomimetics could serve as recognition elements in place of 16–20; a host of polar hydrophilic segments, either peptide- or non-peptide based, could function as amyloid disrupting agents.

We claim:

1. Aβ-amyloid inhibitor compound comprising amino acids 1–12 of SEQ ID NO: 10.

2. The inhibitor compound of claim 1 which is SEQ ID NO: 10.

3. The inhibitor compound of claim 1 which is SEQ ID NO: 11.

4. A pharmaceutical composition comprising the inhibitor compound of claim 1.

5. A pharmaceutical composition comprising the inhibitor compound of claim 2.

6. A pharmaceutical composition comprising the inhibitor compound of claim 3.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Lys Leu Val Phe
1
```

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Lys Leu Val Phe Phe
1               5
```

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Lys Leu Val Phe Phe Ala Glu Asp Val Gly
1               5                   10
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Val Phe Phe Ala Glu Asp Val Gly
1               5
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Phe Phe Ala Glu Asp Val Gly
1               5
```

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Phe Ala Glu Asp Val Gly
1               5

(2) INFORMATION FOR SEQ ID NO:7:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:7:

Val Leu Phe Lys Phe
1               5

(2) INFORMATION FOR SEQ ID NO:8:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:8:

Lys Leu Val Phe Phe Lys Lys Lys Lys Lys Lys
1               5                  10

(2) INFORMATION FOR SEQ ID NO:9:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:9:

Phe Ala Glu Asp Val Gly Lys Lys Lys Lys Lys Lys
1               5                  10

(2) INFORMATION FOR SEQ ID NO:10:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 13..14
         (D) OTHER INFORMATION: /note= "amino caproate should
             appear between residues 13 and 14."

(xi) SEQUENCE DESCRIPTION: SEQ ID NO:10:

Gly Gln Lys Leu Val Phe Phe Ala Glu Asp Val Gly Gly Ala Lys Lys
1               5                  10                  15

Lys Lys Lys Lys
            20

```
(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Lys Lys Lys Lys Lys Lys Gly Gly Gln Lys Leu Val Phe Phe Ala Glu
1               5                   10                  15

Asp Val Gly
```